(12) United States Patent
Levin

(10) Patent No.: US 6,217,580 B1
(45) Date of Patent: Apr. 17, 2001

(54) METHODS OF CLOSING A PATIENT'S STERNUM FOLLOWING MEDIAN STERNOTOMY

(75) Inventor: L. Scott Levin, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/375,527

(22) Filed: Aug. 17, 1999

Related U.S. Application Data

(62) Division of application No. 08/900,667, filed on Jul. 25, 1997, now Pat. No. 6,007,538.

(51) Int. Cl.$^7$ ................................................. A61B 17/80
(52) U.S. Cl. ................................................................ 606/71
(58) Field of Search .................................. 606/60, 69, 70, 606/71, 72, 74

(56) References Cited

U.S. PATENT DOCUMENTS

| | | | |
|---|---|---|---|
| 1,784,716 | * 12/1930 | West | 248/313 |
| 2,208,860 | * 7/1940 | Smart | 248/313 |
| 2,966,907 | 1/1961 | Fasolino . | |
| 3,659,595 | * 5/1972 | Haboush | 606/71 |
| 4,201,215 | 5/1980 | Crossett et al. . | |
| 4,512,346 | 4/1985 | Lemole . | |
| 4,802,477 | 2/1989 | Gabbay . | |
| 4,813,416 | 3/1989 | Pollak et al. . | |
| 4,957,496 | * 9/1990 | Schmidt | 606/70 |
| 5,356,412 | 10/1994 | Golds et al. . | |
| 5,356,417 | 10/1994 | Golds . | |
| 5,423,821 | 6/1995 | Pasque . | |
| 5,549,683 | 8/1996 | Bonutti . | |
| 5,620,444 | 4/1997 | Assaker . | |
| 5,709,684 | * 1/1998 | Errico et al. | 606/61 |
| 5,849,012 | * 12/1998 | Abboudi | 606/74 X |
| 5,928,231 | * 7/1999 | Klein et al. | 606/60 |
| 6,007,538 | * 12/1999 | Levin | 606/71 |

FOREIGN PATENT DOCUMENTS

96/36291 * 11/1996 (WO) ............................. A61B/17/68

OTHER PUBLICATIONS

Hendrickson et al, "Sternal Plating for the Treatment of Sternal Nonunion", *Ann Thorac Surg*, 1966; 62:512–8.

* cited by examiner

Primary Examiner—Jeffrey A. Smith
(74) Attorney, Agent, or Firm—Nixon & Vanderhye P.C.

(57) ABSTRACT

Sternal clamping devices have a pair of opposed generally J-shaped clamp members which are laterally adjustable relatively to one another but can be rigidly joined via a set of machine screws. Preferably, the machine screws are of a taper-headed variety which seat within a conformably shaped countersunk region of one of the clamp members so as to present a substantially flush upper surface. The machine screws are, however, of sufficient length so as to be coupled threadingly with a respective threaded aperture formed in the other clamp member. The threaded coupling of the set screws with the other clamp member will thus rigidly unite the pair of clamp members one to another without lateral shifting occurring over time. Also, the clamp members may be rapidly disassembled and separated from one another (e.g., in case of a medical emergency requiring the surgeon to have quick access to the patient's thoracic cavity) by simply removing the set of screws therefrom.

9 Claims, 3 Drawing Sheets

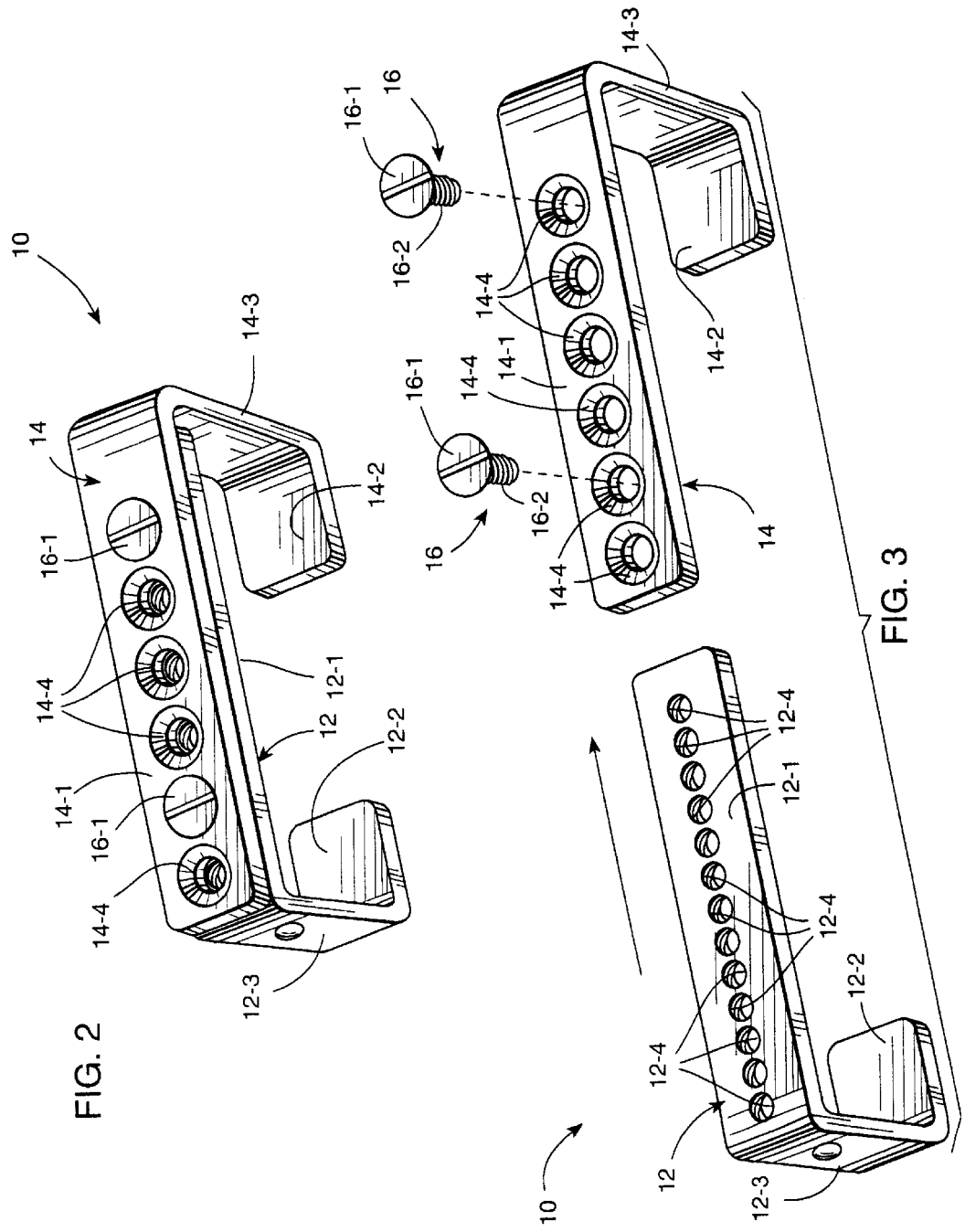

METHODS OF CLOSING A PATIENT'S STERNUM FOLLOWING MEDIAN STERNOTOMY

This is a divisional of application Ser. No. 08/900,667, filed Jul. 25, 1997, now U.S. Pat. No. 6,007,538.

FIELD OF THE INVENTION

The present invention relates generally to surgical devices. More specifically, the present invention relates to the field of devices employed to reapproximate a patient's sternum following a median sternotomy.

BACKGROUND AND SUMMARY OF THE INVENTION

Surgical procedures involving tissue or organs located in a patient's thoracic cavity (e.g., heart, lungs and the like) typically require a median sternotomy. That is, in order to gain access to tissue or organs located in a patient's thoracic cavity, it is oftentimes necessary for a midline sternal incision is made to allow the sternum to be separated laterally. After the surgical procedure is performed, the sternum must be reapproximated (i.e., closed). Conventionally, such reapproximation of the patient's sternum has involved using surgical stainless steel wires wrapped around (or through) the sternal halves so as to exert medial compression thereon. The wires are typically left in place permanently, unless a postoperative problem is encountered, in which case, a follow-up surgical procedure is performed to remove them. In this regard, a certain percentage of sternotomy patients experience chronic sternal pain postoperatively as a consequence of sternal nonunion due to inadequate sternal stability of the surgical wires.

Attempts have been made to offer substitutes for conventional surgical wiring techniques as evidenced by U.S. Pat. No. 4,201,215 to Crossett et al (hereinafter "Crossett et al '215), the entire contents of which are incorporated expressly hereinto by reference. According to the Crossett et al '215 patent, a sternum clamp is provided having a pair of elongate planar clamping members, each of which includes a clamping hook at one end thereof. One of the clamping members is provided with turned over, opposed lateral flanges defining guide groves which slidably receive a portion of the other clamping member. Thus, with the clamping hooks positioned in lateral engagement with a respective one of the patient's sternal halves, an end of the other clamping member may be brought into slidable engagement with the guide groove flanges. Thereafter, the guide groove flanges are crimped causing the device to bow slightly and thereby postionally lock the clamping members one to another.

Some potential problems may arise, however, using the sternal clamp disclosed in the Crossett et al '215 patent. For example, the positional restraint provided by the crimped guide groove flanges may not be sufficient in order to reliably laterally fix the clamp members one to another. That is, over time, it is entirely possible that the crimps could wear somewhat thereby reducing their frictional engagement with the clamp members. Furthermore, the crimps may not be sufficient to withstand the inherent lateral bias forces of the sternal halves over time. (Perhaps this is one reason why Crossett et al '215 additionally suggest the use of retaining wires threaded through holes formed in the sternal halves.) Any lateral shifting of the clamp members, and the resultant separation/movement of the patient's severed sternum could quite possibly create acute pain for the patient—a clearly undesirable effect.

On the other hand, the crimped guide groove flanges of the Crossett et al '215 device could possibly be difficult to uncrimp and/or otherwise loosen if separation of the clamping members were desired. Any such difficulties in separating the clamping members could therefore be quite problematic to an attending physician if a medical emergency arose during the procedure requiring relatively quick access to the organs and/or tissues of the patient's thoracic cavity, such as emergency sternal reopening after surgery for purposes of hemorrhage control and/or open heart massage.

In view of the problems identified above, improvements to sternal clamping devices generally are clearly needed. It is towards providing such improvements that the present invention is directed.

Broadly, the present invention is embodied in a separable sternal clamping device. Preferably, the sternal clamping device has a pair of opposed generally J-shaped clamp members which are laterally adjustable relatively to one another but can be rigidly joined, for example, via a set of machine screws. The machine screws most preferably are of a taper-headed variety which seat within a conformably shaped countersunk region of one of the clamp members so as to present a substantially flush upper surface. The machine screws are, however, of sufficient length so as to be coupled threadingly with a respective threaded aperture formed in the other clamp member. The clamp member and screws are most preferably formed of medical grade stainless steel.

The threaded coupling of the set screws with the other clamp member will thus rigidly unite the pair of clamp members one to another without lateral shifting occurring over time. Also, the clamp members may be rapidly disassembled and separated from one another (e.g., in case of a medical emergency requiring the surgeon to have access to the patient's thoracic cavity) by simply removing the set of screws therefrom.

These and other aspects and advantages of the present invention will become more clear after careful consideration is given to the following detailed description of the preferred exemplary embodiments thereof.

BRIEF DESCRIPTION OF THE ACCOMPANYING DRAWINGS

Reference will hereinafter be made to the accompanying drawings wherein like reference numerals throughout the various FIGURES denote like structure elements, and wherein:

FIG. 2 is a perspective view of the sternal closure device shown in an assembled state;

FIG. 3 is a perspective view of the sternal closure device of this invention shown in a disassembled state.

DETAILED DESCRIPTION OF THE INVENTION

Figure 1:
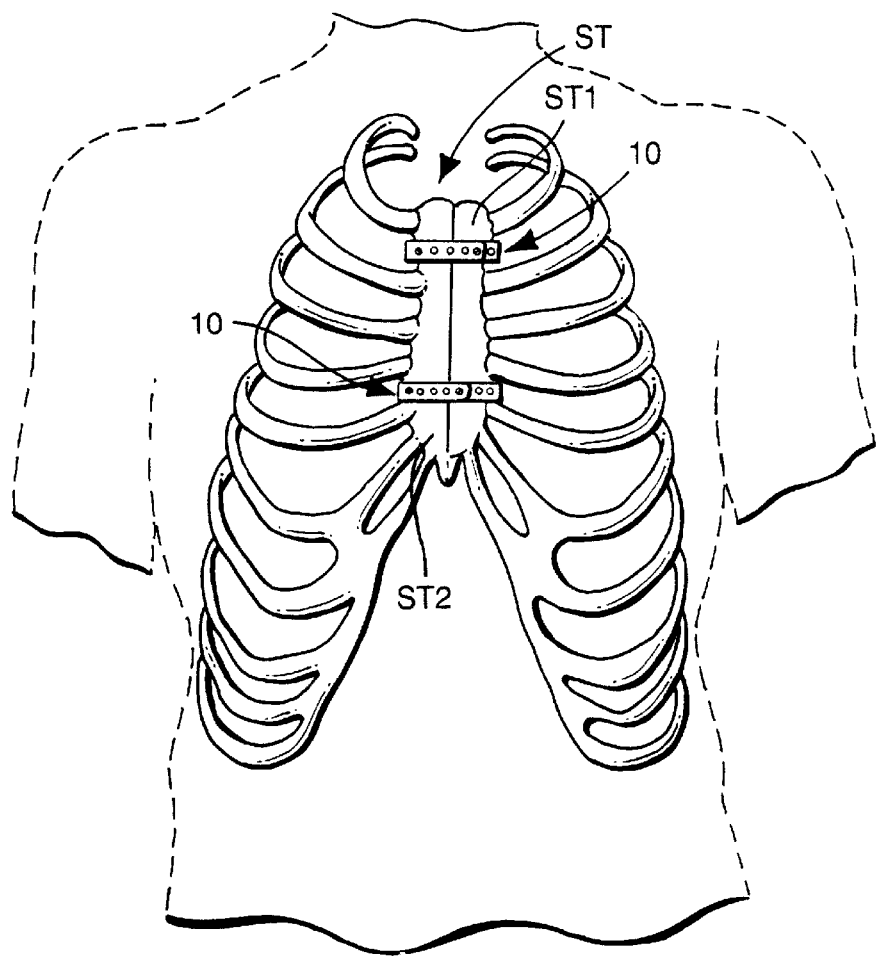
FIG. 1 is a schematic postoperative anterior view of a patient's sternum and associated ribs showing one possible placement scheme for the sternal closure devices according to the present invention.

Accompanying FIG. 1 shows in schematic fashion an anterior view of a patient's sternum ST following a median sternotomy. Specifically, as shown, the sternal halves ST1 and ST2 of patient's sternum ST are reapproximated using a pair of sternal closure devices 10 in accordance with the present invention. The devices 10 are clamped laterally around each of the sternal halves ST1, ST2 and thus exert medial compressive force thereon so as to reapproximate the sternum ST.

An exemplary sternal closure device 10 is depicted in accompanying FIGS. 2 and 3. As shown therein, the device includes a pair of opposed generally J-shaped clamp members 12, 14 each being respectively comprised of an elongate planar spanning leg 12-1, 14-1, a hook leg 12-2, 14-2 spaced from, but substantially parallel to, the spanning leg 12-1, 14-1, and a lateral support leg 12-3, 14-3 rigidly joined to the legs 12-1, 12-2 and 14-1, 14-2 at substantially right angles thereto. Most preferably the clamp members 12, 14 are formed from medical grade stainless steel bar stock (e.g., 316L) with bends therein to establish the legs 12-1 through 12-3 and 14-1 through 14-3. Since the device 10 is constructed of stainless steel, it may be permanently implanted in patients, if required.

The clamp member 14 is provided with a series of through apertures 14-4 each having generally conically shaped countersunk surfaces for conformably receiving the generally conically shaped tapered head 16-1 of a respective machine screw 16. The apertures 14-4 are axially aligned in the lengthwise direction of leg 14-1. The other clamp member 12 includes a series of threaded through apertures 12-4 adapted to threadingly receive the threaded shank 16-2 of a respective set screw 16. The threaded apertures 12-4 are aligned axially in the lengthwise direction of the leg 12-1.

Since the set screws 16 are of the taper-headed variety and thus are received within the conformably shaped conical countersunk surface of the apertures 14-4, the head of the screw will be flush with the external surface of the spanning leg 14-1. As a result, the screws 16 will not be an irritant to the surrounding tissue postoperatively.

As can be appreciated pairs of apertures 12-4, 14-4 may be brought into vertical registration with one another in dependence upon the relative position of the clamp members 12, 14. As such, the lateral dimension between the opposed support legs 12-3, 14-3 can be adjustably selected to fit a particular patient's sternum. The set screws 16 may then be threadably engaged as noted above in respective one of the registered aperture pairs 12-4, 14-4 so as to rigidly unite the clamp members 12,14.

While the lateral sizing of the clamp members 12, 14 may be selectively adjusted based on the relative positioning of the legs 12-1, 14-1, the "depth" dimension of the clamp members 12, 14 is fixed by virtue of the dimension of the support legs 12-3, 14-3, respectively. Therefore, it is presently preferred to provide the attending surgeon with a range of possible clamp member sizes so as to accommodate a particular patient's sternal anatomy. However, the patient's sternal anatomy may also be determined preoperatively by non-invasive imaging techniques (such as via three-dimensional computed tomography (ct) scan) so that a custom-sized clamp member may be fabricated in advance of the surgical procedure.

Figure 4A:
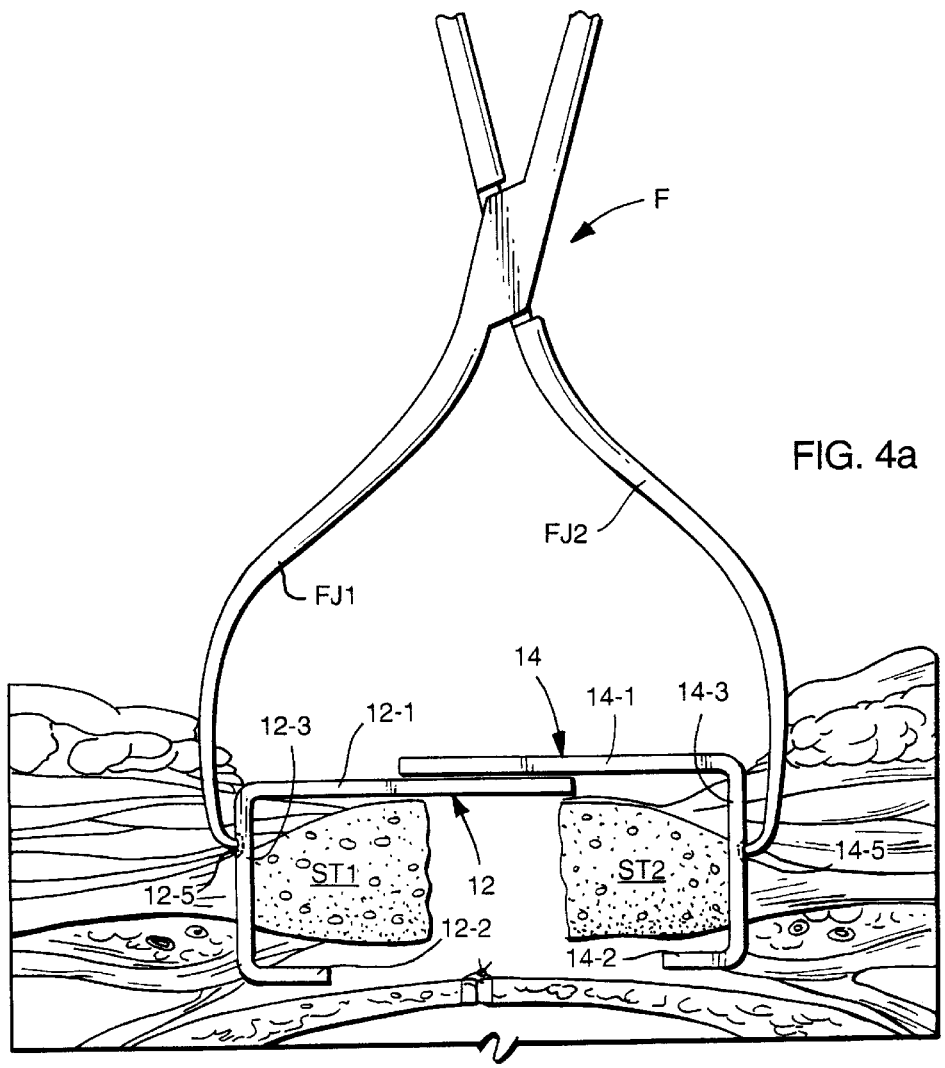
FIGS. 4a and 4b are schematic transverse sectional views depicting a preferred sequence employed to reapproximate a patient's sternum using the sternal closure device of this invention.
Figure 4B:
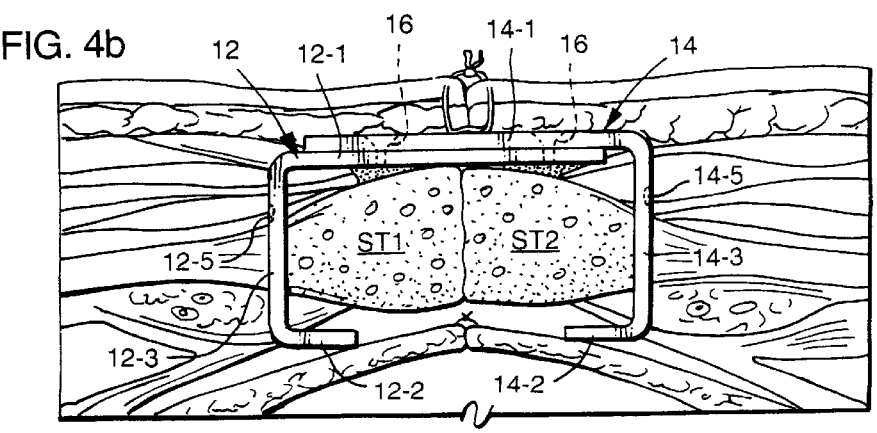

Accompanying FIGS. 4a and 4b depict schematically a sternal reapproximation procedure employing the sternal closure device 10 according to the present invention. As shown, during the sternal reapproximation procedure, the members 12, 14 will be hooked laterally around the sternal halves ST1, ST2, respectively, with their respective spanning legs 12-1, 14-1 in overlapping relationship to one another—that is, with the spanning leg 14-1 of clamp member 14 superposed with the spanning leg 12-1 of clamp member 12. As depicted in FIG. 4a, during the reapproximation procedure, the attending surgeon may be aided by surgical forceps F having jaws EJ1 and EJ2 engaged with recesses or dimples 12-5, 14-5 on an exterior surface of the legs 12-3, 14-3. Once the sternal halves ST1, ST2 have been closed, the set screws 16 are inserted into a pair of apertures 12-4, 14-4 and threadably coupled thereto so as to rigidly unite the clamp members 12, 14. The surrounding muscle tissue and the like may thereafter be closed using conventional sutures, surgical staples or the like. As noted previously, typically a plurality of such sternal closure devices 10 will be needed in order to reapproximate the patient's sternum as determined by the attending surgeon's professional judgment.

If there is any need to remove the device 10 (e.g., due to an emergency requiring the physician to gain access to the patient's thoracic cavity), the screws 16 may simply and quickly be threadably removed from the apertures 12-4, 14-4 so that the clamp members 12, 14 (and the sternal halves ST1, ST2) can be separated laterally away from one another. However, as noted previously, the device 10 may remain permanently implanted in the patient if deemed necessary by the attending physician.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of closing a patient's sternum following a median sternotomy comprising:
    (a) placing generally J-shaped clamp members about a respective sternal half;
    (b) bringing opposed legs of each clamp member into overlapping relationship to one another; and
    (c) removably securing said opposed overlapping legs one to another.

2. The method of claim 1, wherein step (c) including joining said opposed legs one to another by means of a machine screw.

3. The method of claim 1, wherein step (b) including forcibly closing the clamp members following placement of the clamp members about a respective sternal half according to step (a).

4. The method of claim 3, wherein step (b) includes using a forceps.

5. The method of claim 4, comprising placing jaws of the forceps in respective recessed dimples.

6. A method of closing a patient's sternum following a median sternotomy comprising the steps of:
- (a) providing a sternal closure device comprising a pair of generally opposed J-shaped clamp members sized and configured to conform substantially to the patient's sternal anatomy;
- (b) placing the J-shaped clamp members about a respective opposed portion of the patient's sternum; and
- (c) rigidly, but removably, joining opposed leg members of the J-shaped clamp members to one another, whereby the patient's sternum is closed.

7. The method of claim 6, wherein step (b) includes overlapping the opposed leg members of the J-shaped clamp members.

8. The method of claim 7, wherein the leg member of one of the clamp members includes through holes which are non-threaded for receiving a head of a set screw, and the leg member of another one of the clamp members includes through holes which are threaded for receiving a threaded shank of the set screw, and wherein step (b) includes registering through holes of said one and another clamp members, and wherein step (c) threadably coupling the leg members to one another by a set screw received within at least one of the registered through holes.

9. The method of claim 6, wherein step (b) includes forcibly closing the clamp members following placement of the clamp members about a respective portion of the patient's sternum.

\* \* \* \* \*